United States Patent [19]

Theodoridis

[11] Patent Number: 4,816,065
[45] Date of Patent: Mar. 28, 1989

[54] HERBICIDES

[75] Inventor: George Theodoridis, Princeton, N.J.

[73] Assignee: FMC Corporation, Philadelphia, Pa.

[21] Appl. No.: 945,933

[22] Filed: Dec. 23, 1986

[51] Int. Cl.$^4$ .............. A01N 43/40; A01N 43/38; C07D 401/02; C07D 209/48
[52] U.S. Cl. .............................. 71/94; 71/96; 546/272; 548/513
[58] Field of Search ............ 548/513; 546/272; 71/94, 95, 96

[56] References Cited

U.S. PATENT DOCUMENTS

| | | | |
|---|---|---|---|
| 3,954,442 | 5/1976 | Becker et al. | 71/108 |
| 4,292,070 | 9/1981 | Wakabayashi et al. | 71/96 |
| 4,332,944 | 6/1982 | Anderson et al. | 71/94 |
| 4,426,220 | 1/1984 | Parg et al. | 71/108 |
| 4,439,229 | 3/1984 | Swithenbank | 548/513 |
| 4,490,165 | 12/1984 | Spatz et al. | 71/108 |
| 4,514,210 | 4/1985 | Aya et al. | 71/92 |
| 4,550,192 | 10/1985 | Rogers et al. | 71/108 |
| 4,618,365 | 10/1986 | Covey et al. | 71/92 |

FOREIGN PATENT DOCUMENTS

| | | | |
|---|---|---|---|
| 3533442 | 3/1987 | Fed. Rep. of Germany | 548/513 |
| 160447 | 8/1983 | German Democratic Rep. | |
| WO8501939 | 5/1985 | PCT Int'l Appl. | |

Primary Examiner—Mary E. Ceperley
Attorney, Agent, or Firm—Robert M. Kennedy; H. Robinson Ertelt; Abner Sheffer

[57] ABSTRACT

Herbicidal compounds, compositions containing them, and a method for controlling weeds by application of the compositions are disclosed. The herbicidal compounds are N-aryl tetrahydrophthalimides of the formula

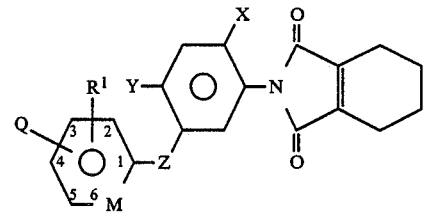

in which Z is O, S, NH or alkylamino; Q is —[O—CH(-R$^{4a}$)CO]$_m$—OCH(R$^4$)Q$^2$; Q$^2$ is —C(O)R$^3$ or —CN; M is CH or N; R$^4$ and R$^{4a}$ are independently H, C$_2$H$_5$ or CH$_3$; R$^3$ is OH, alkoxy, alkylthio, alkenyloxy or alkynyloxy, amino, phenylamino, alkylamino, alkenylamino, alkynylamino, alkoxyamino or alkyl-, haloalkyl- or arylsulfonylamino of the formula —NHSO$_2$R$^5$ or —N(SO$_2$R$^5$)SO$_2$R$^6$, or an —O—N=R$^7$ radical where R$^7$ is alkylidene; R$^5$ and R$^6$ are indendently alkyl, haloalkyl or phenyl which is unsubsituted or substituted with alkoxy or halogen; m is zero or 1; R$^1$ is H, alkyl, halogen, haloalkyl, nitro, NH$_2$, alkoxy or alkylthio, or cyano; X is H, halogen, alkyl, haloalkyl or nitro; and Y is H, halogen, alkyl, alkoxy, haloalkyl, —SOCF$_3$ or haloalkoxy.

12 Claims, No Drawings

HERBICIDES

This invention relates to novel herbicides for weed control in agriculture, horticulture and other fields where it is desired to control unwanted plant growth, such as grassy or broadleaf plant species. The information also relates to intermediates for the production of herbicides.

One aspect of this invention relates to herbicidal compounds of the formula (Formula I)

where Z may be O, S, NH or alkylamino (such as lower alkylamino, e.g. methylamino) and Q is $$-[O-CH(R^{4a})CO]_m-OCH(R^4)Q^2$$

$Q^2$ is $-C(O)R^3$ or $-CN$.

M is CH or N.

$R^4$ and $R^{4a}$ may be H or $CH_3$ or $C_2H_5$ and $R^3$ may be OH, alkoxy (e.g. lower alkoxy such as methoxy or ethoxy) alkylthio (e.g. lower alkylthio such as thiomethyl), lower alkenyloxy or alkynyloxy (e.g. allyloxy or propargyloxy), amino, arylamino (e.g. phenylamino), alkylamino (e.g. lower alkylamino such as methylamino or dimethylamino), alkenylamino (e.g. diallylamino), alkynylamino (e.g. proparpylamine), alkoxyamino (e.g. lower alkoxyamino such as methoxyamino) or alkyl-, haloalkyl- or arylsulfonylamino of the formula $-NHSO_2R^5$ or $-N(SO_2R^5)SO_2R^6$, or an $-O-N=R^7$ radical where $R^7$ is alkylidene (e.g. lower alkylidene such as isopropylidene).

$R^5$ and $R^6$ may be independently alkyl (e.g. lower alkyl such as methyl, ethyl or propyl), haloalkyl (e.g. halo lower alkyl such as trifluoromethyl) or aryl such as phenyl or substituted phenyl, (e.g. alkoxy-substituted and/or halo-substituted phenyl).

"m" may be zero or 1.

$R^1$ may be H, alkyl (e.g. lower alkyl such as methyl), halogen such as Cl, Br or F, haloalkyl (e.g. lower haloalkyl such as $CF_3$, $CH_2F$ or $CHF_2$), nitro, $NH_2$, lower alkoxy or alkylthio (e.g. $OCH_3$ or $SCH_3$) or cyano. There may be a plurality of $R^1$ substituents on the same benzene ring.

X may be H, halogen such as Cl, Br or F (preferably F), alkyl (e.g. lower alkyl such as methyl), haloalkyl (e.g. lower haloalkyl such as $CF_3$, $CH_2F$ or $CHF_2$) or nitro; and Y may be H, halogen such as Cl, Br or F (preferably Br or Cl), alkyl (e.g. lower alkyl such as methyl), alkoxy (e.g. lower alkoxy such as methoxy), haloalkyl (e.g. lower haloalkyl such as fluoroalkyl), $-SOCF_3$ or halo lower alkoxy such as $-OCHF_2$. Presently preferred X, Y substituents are: 2-F, 4-Cl; 2-F, 4-Br; 2,4-Cl; 2Br, 4-Cl; and 2F, 4-$CF_3$.

In each aspect of the invention it is often preferable that any alkyl, alkenyl, alkynyl or alkylene moiety (such as the hydrocarbon moiety of an alkoxy or haloalkoxy group) have less than 6 carbon atoms, e.g. 1 to 3 carbon atoms.

Any acidic compound of formula I may be converted into a salt such as a sodium, potassium, calcium, ammonium, magnesium, or mono-, di- or tri($C_1$ to $C_4$ alkyl)ammonium or sulfonium or sulfoxonium salt which may also be used as an herbicide.

Representative compounds of this invention (including certain intermediates) are listed in Table 1.

The compounds of this invention may be prepared by the use of steps generally described in the literature or in the following Examples or by methods analogous or similar thereto and within the skill of the art. In Example 1 below, the starting material is a hydroxyphenyl tetrahydrophthalimide (specifically compound III of U.S. Pat. No. 4,431,822). In Example 2, the tetrahydrophthalimide is formed at an intermediate stage in the process, from a hydroxyphenylether of a substituted aniline, after which the hydroxy group is etherified.

EXAMPLE 1

ETHYL 2-[4-[2-CHLORO-4-FLUORO-5-(3,4,5,6-TETRAHYDROPHTHALIMIDO-1-YL)PHENOXY]PHENOXY]PROPIONATE

Step A 1-(4-Chloro-2-fluoro-5-hydroxyphenyl)-3,4,5,6-tetrahydrophthalimide

Hydrogenatin of 10.0 g (0.052 mole) of 4-chloro-2-fluoro-5-hydroxynitrobenzene with a catalytic amount (0.3 g) of platinum oxide in 100 mL of ethanol produced 4-chloro-2-fluoro-5-hydroxyaniline. Subsequently this aniline was dissolved in 100 mL of glacial acetic acid and 7.60 g (0.050 mole) of 3,4,5,6-tetrahydrophthalic anhydride was added. The resultant mixture was stirred and heated at reflux for approximately 18 hours. The reaction mixture was poured into ice water forming a precipitate which was collected by filtration to yield 9.90 g of 1-(4-chloro-2-fluoro-5-hydroxyphenyl)-3,4,5,6-tetrahydrophthalimide, m.p. 140°–141° C.

Step B

1-[4-Chloro-2-fluoro-5-(4-nitrophenoxy)phenyl]-3,4,5,6-tetrahydrophthalimide

A solution of 9.90 g (0.033 mole) of 1-(4-chloro-2-fluoro-5-hydrophenyl)-3,4,5,6-tetrahydrophthalimide in 40 mL of N,N-dimethylformamide was added slowly to a stirred mixture of sodium hydride (1.53 g of a 50% suspension in mineral oil) in 50 mL of dimethylformamide. The mixture was stirred at room temperature for one hour and 4.66 g (0.033 mole) of 4-fluoronitrobenzene was added. This mixture was stirred at room temperature for approximately 18 hours, then heated at 80° C. for five hours. The mixture was cooled to room temperature and poured into 300 mL of ice water containing 10 mL of concentrated hydrochloric acid. The resultant aqueous mixture was extracted with diethyl ether. The extract was dried over anhydrous magnesium sulfate and filtered. The filtrate was evaporated under reduced pressure leaving a residue. Purification of this residue by column chromatography yielded 5.0 g of 1-[4-chloro-2-fluoro-5-(4-nitrophenoxy)phenyl]-3,4,5,6-tetrahydrophthalimide as a solid, m.p. 126° C.

This reaction was repeated to obtain additional 1-[4-chloro-2-fluoro-5-(4-nitrophenoxy)phenyl]-3,4,5,6-tetrahydrophthalimide.

Step C

1-[5-(4-Aminophenoxy)-4-chloro-2-fluorophenyl]-3,4,5,6-tetrahydrophthalimide To a stirred solution of 20 mL of water in 200 mL of glacial acetic acid was added 6.0 g (0.014 mole) of 1-[4-chloro-2-fluoro-5-(4-nitrophenoxy)phenyl]-3,4,5,6-tetrahydrophthalimide. This mixture was stirred at room temperature while 6.0 g (0.11 mole) of iron filings were slowly added. After complete addition the mixture was stirred at room temperature for one hour. Diethyl ether was added and the resultant mixture was filtered through a pad of celite. The filtrate was washed with 200 mL of water. The organic phase was dried over anhydrous magnesium sulfate and filtered. The filtrate was evaporated under reduced pressure leaving a solid. This solid was purified by column chromatography on silica gel, eluting with methylene chloride, to yield 4.0 g of 1-[5-(4-aminophenoxy)-4-chloro-2-fluorophenyl]-3,4,5,6-tetrahydrophthalimide as a solid, m.p. 213°–215° C.

Step D

1-[4-Chloro-2-fluoro-5-(4-hydroxyphenoxy)phenyl]-2,3,4,5-tetrahydrophthalimide While maintaining a temperature of 20°–25° C., 1.7 g (0.0040 mole) of 1-[5-(4-aminophenoxy)-4-chloro-2-fluorophenyl]-3,4,5,6-tetrahydrophthalimide was added to 4.0 mL of stirred, concentrated sulfuric acid. To this was added a solution of 0.40 g (0.0055 mole) of sodium nitrite dissolved in 6 mL of water, while continuing to maintain a temperature of about 20° C. After complete addition, the mixture was stirred at 20° C. for 30 minutes. This mixture was added through a glass tube to the bottom of a stirred, refluxing mixture of 30.0 g (0.120 mole) of copper (II) sulfate pentahydrate, 90 mL of water and 30 mL of xylene. After complete addition the mixture was refluxed for one hour. The mixture was cooled, and the organic phase was extracted with an aqueous, sodium hydroxide solution (6.0 g of sodium hydroxide dissolved in 250 mL of water). The basic extract was acidified with concentrated hydrochloric acid and was extracted with diethyl ether. The organic extract was dried over anhydrous magnesium sulfate and filtered. The filtrate was evaporated to yield 0.6 g of 1-[4-chloro-2-fluoro-5-(4-hydroxyphenoxy)phenyl]-2,3,4,5-tetrahydrophthalimide as an oil.

Step E

Ethyl 2-[4-[2-chloro-4-fluoro-5-(3,4,5,6-tetrahydrophthalimido-1-yl)phenoxy]phenoxy]propionate A stirred mixture of 0.50 g (0.0013 mole) of 1-[4-chloro-2-fluoro-5-(4-hydroxypheoxy)phenyl]-2,3,4,5-tetrahydrophthalimide, 0.36 g (0.0026 mole) of ethyl 2-bromopropionate in 40 mL of acetone was heated at reflux for approximately 18 hours. The mixture was cooled and filtered. The filtrate was evaporated under reduced pressure leaving a residue. This residue was purified by column chromatography on silica gel, eluting with methylene chloride, to yield 0.30 g of ethyl 2-[4-2-chloro-4-fluoro-5-(3,4,5,6-tetrahydrophthalimido-1-yl)phenoxy]phenoxy]propionate as an oil.

The nmr spectrum was consistent with the proposed structure.

EXAMPLE 2

ETHYL 2-[4-[2-CHLORO-4-FLUORO-5-(3,4,5,6-TETRAHYDROPHTHALIMIDO-1-YL)PHENOXY]-PHENOXY]ACETATE

Step A

4-Chloro-2-fluoro-5-hydroxyacetanilide

Hydrogenation of 30.0 g (0.16 mole) of 4-chloro-2-fluoro-5-hydroxynitrobenzene with a catalytic amount (0.3 g) of platinum oxide in 100 mL of ethanol produced a solid residue. This reidue was stirred in a solution of acetic anhydride (20.0 ml, 0.20 mole) and water (200 mL). This mixture was stirred for a short period then was filtered. The filter cake was dried to yield 26.0 g of 4-chloro-2-fluoro-5-hydroxyacetanilide as a solid, m.p. 210°–212° C.

Step B

4-Chloro-2-fluoro-5-(4-nitrophenoxy)acetanilide

To a stirred mixture of 17.7 g (0.128 mole) of potassium carbonate in 100 mL of N,N-dimethylformamide was added 26.0 g (0.128 mole) of (4-chloro-2-fluoro-5-hydroxyacetanilide. The mixture was heated at 50° C. to 60° C. for two days then at 70° C. to 80° C. for two hours. The mixture was cooled and poured into ice water. A precipitate formed and was collected by filtration to yield 29.0 g of 4-chloro-2-fluoro-5-(4-nitrophenoxy)acetanilide m.p. 140°–142° C.

Step C

5-(4-Aminophenoxy)-4-chloro-2-fluoroacetanilide

Hydrogenation of 28.5 g (0.0948 mole) of 4-chloro-2-fluoro-5-(4-nitrophenoxy)acetanilide with a catalytic amount (0.3 g) of platinum oxide in 150 mL of ethanol produced 22.3 g of 5-(4-aminophenoxy)-4-chloro-2-fluoroacetanilide as a solid, m.p. 163°–166° C.

Step C

4-Chloro-2-fluoro-5-(4-hydroxyphenoxy)acetanilide

In a manner similar to that of Step D of Example 1, a solution of 22.3 (0.076 mole) of 5-(4-aminophenoxy)-4-chloro-2-fluoroacetanilide in 60 mL of concentrated sulfuric acid and 30 g of ice was treated with an aqueous solution of 5.25 g (0.076 mole) of sodium nitrite in 30 mL of water. This mixture was added to a refluxing mixture of 160 g (0.64 mole) of copper (II) sulfate in 300 mL of water and 200 mL of xylene. This mixture was cooled to room temperature, and the organic phase was separated from the aqueous phase. The aqueous phase was extracted with ethyl acetate. The extract and organic phase were combined and dried over anhydrous magnesium sulfate. This mixture was filtered and the filtrate was evaporated under reduced pressure leaving a residue. This residue was purified by column chromatography on silica gel, eluting with methylene chloride-:ethyl acetate (80:20), to yield 6.5 g of 4-chloro-2-fluoro-5-(4-hydroxyphenoxy)acetanilide as a solid, m.p. 141°–144° C.

Step E

1-[4-Chloro-2-fluoro-5-(4-hydroxyphenoxy)phenyl]-3,4,5,6-tetrahydrophthalimide A stirred mixture of 5.85 g (0.0231 mole) of 4-chloro-2-fluoro-5-(4-hydroxyphenoxy)acetanilide and 3.20 g (0.0216 mole) of phthalic anhydride in 50 mL of glacial acetic acid was heated at reflux for approximately 18 hours. The mixture was cooled to room temperature and poured into ice water. A precipitate formed and was collected by filtration. This solid was purified by column chromatography on silica gel, eluting with methylene chloride, to yield 6.1 g of 1-[4-chloro-2-fluoro-5-(4-hydroxyphenoxy)phenyl]-3,4,5,6-tetrahydrophthalimide as a solid, m.p. 117°–120° C.

Step F

Ethyl 2-[4-[2-chloro-4-fluoro-5-(3,4,5,6-tetrahydrophthalimido-1-yl)phenoxy]phenoxy]acetate In a manner similar to Step E of Example 1, the reaction of 0.70 g (0.0018 mole) of 1-[4-chloro-2-fluoro-5-(4-hydroxyphenoxy)phenyl]-3,4,5,6-tetrahydrophthalimide with 0.25 g (0.0018 mole) of potassium carbonate and 0.60 g (0.0036 mole) of ethyl bromoacetate in 25 mL of acetone produced 0.43 g of ethyl 2-[4-[2-chloro-4-fluoro-5-(3,4,5,6-tetrahydrophthalimido-1-yl)phenoxy]phenoxy]acetate as a solid, m.p. 102°–103° C.

The nmr spectrum was consistent with the proposed structure.

The herbicidal data in the following Tables 3 and 4 was obtained in the manner described in PCT published application no. WO 85/01939, published 5/9/85, usually employing solutions of the herbicidal compound in 50/50 acetone/water mixtures. In those tables, the test compounds are identified by numbers which correspond to those in Table 1, "kg/ha" is kilograms per hectare, and "% C" is percent control.

For herbicidal application, the active compounds are formulated into herbicidal compositions by admixture in herbicidally effective amounts with adjuvants and carries normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules (e.g. for paddy rice) in the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Other wettable power formulations are:

| Component: | % by Wt. |
|---|---|
| Active ingredient | 40.00 |
| Sodium ligninsulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium ligninsulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition. The following are specific examples of emulsifiable concentrate formulations:

| Component: | % by Wt |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component | % by Wt. |
| --- | --- |
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 41.42 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acids esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
| --- | --- |
| Oil Suspension: | |
| Active ingredient | 25.00 |
| polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture.

In applying an active compound of this invention, whether formulated alone or with other agricultural chemicals, an effective amount and concentration of the active compound is, of course, employed; the amount may be below about 500 g/ha and may be as low as, for example 2 g/ha or lower, e.g. about 1 to 250 g/ha preferably about 8 to 60 g/ha. Favorable selectivity has been shown for crops such as soybeans and wheat, and especially for rice and corn.

The active herbicidal compounds of this invention may be used in combination with other herbicides, e.g. they may be mixed with, say, an equal or larger amount of a known hericide such as chloroacetanilide herbicides such as 2-chloro-N-(2,6-diethylphenyl)-N-(methoxymethyl)acetamide (alachlor), 2-chlor-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methyl-propanenitrile (cyanazine); dinitrolaniline herbicides such as 2,6-dinitro-N,N-dipropyl-4-(trifluoromethyl)-benzenaeamine (trifluralin); and aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidone.

It is apparent that various modifications may be made in the formulation and application of the compounds of this invention without departing from the inventive concepts herein as defined in the claims.

TABLE 1

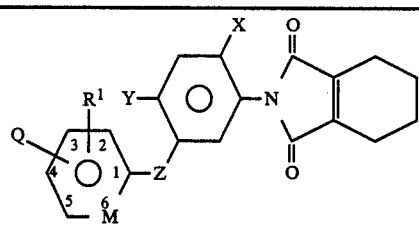

where Q is $-[O-CH(R^{4a})CO]_m-OCH(R^4)Q^2$, m is zero and M is CH.

| Cmpd. No. | X | Y | Z | $R^1$ | $R^4$ | $Q^2$ | Position of Q |
|---|---|---|---|---|---|---|---|
| 1 | F | Cl | O | H | $CH_3$ | $C(O)OC_2H_5$ | 4 |
| 2 | F | Cl | O | H | H | $C(O)OC_2H_5$ | 4 |
| 3 | F | Cl | O | H | $CH_3$ | $C(O)OCH_3$ | 4 |
| 4 | Cl | Cl | O | H | $CH_3$ | $C(O)OC_2H_5$ | 4 |
| 5 | Cl | Cl | O | H | H | $C(O)OC_2H_5$ | 4 |
| 6 | Cl | Cl | O | H | H | $C(O)OCH_3$ | 4 |
| 7 | F | Cl | O | H | H | $C(O)OCH_3$ | 4 |
| 8 | F | Cl | O | H | $CH_3$ | $C(O)OH$ | 4 |
| 9 | F | Cl | O | H | $CH_3$ | $C(O)NH_2$ | 4 |
| 10 | F | Cl | O | H | $CH_3$ | $C(O)N(CH_3)_2$ | 4 |
| 11 | F | Cl | O | H | $CH_3$ | $C(O)NH(CH_3)$ | 4 |
| 12 | F | Cl | O | H | $CH_3$ | $C(O)NHSO_2CH_3$ | 4 |
| 13 | F | Br | O | H | $CH_3$ | $C(O)OC_2H_5$ | 4 |
| 14 | F | Cl | O | H | $CH_3$ | $C(O)OCH_2(CH_3)_2$ | 4 |
| 15 | F | Br | O | H | $CH_3$ | $C(O)OCH_2(CH_3)_2$ | 4 |
| 16 | Cl | Cl | O | H | $CH_3$ | $C(O)OCH_2(CH_3)_2$ | 4 |
| 17 | F | Cl | O | H | H | $C(O)OCH_2(CH_3)_2$ | 4 |
| 18 | Cl | Cl | O | H | H | $C(O)OCH_2(CH_3)_2$ | 4 |
| 19 | F | Br | O | H | $CH_3$ | $C(O)OCH_3$ | 4 |
| 20 | F | Br | O | H | $CH_3$ | $C(O)OCH(CH_3)_2$ | 4 |
| 21 | F | Br | O | H | $CH_3$ | $C(O)OH$ | 4 |
| 22 | F | Br | O | H | $CH_3$ | $C(O)NH(SO_2CH_3)$ | 4 |
| 23 | F | Br | O | H | $CH_3$ | $C(O)NH_2$ | 4 |
| 24 | F | Br | O | H | $CH_3$ | $C(O)NH(CH_3)$ | 4 |
| 25 | F | Br | O | H | $CH_3$ | $C(O)N(CH_3)_2$ | 4 |
| 26 | F | Cl | O | 2-Cl | $CH_3$ | $C(O)OCH_3$ | 4 |
| 27 | F | Cl | O | 3-Cl | $CH_3$ | $C(O)OCH_3$ | 4 |
| 28 | F | Cl | O | 2-F | $CH_3$ | $C(O)OCH_3$ | 4 |
| 29 | F | Cl | O | 3-F | $CH_3$ | $C(O)OCH_3$ | 4 |
| 30 | F | Cl | O | 3-$OCH_3$ | $CH_3$ | $C(O)OCH_3$ | 4 |
| 31 | F | Cl | O | 3-$NO_2$ | $CH_3$ | $C(O)OCH_3$ | 4 |
| 32 | F | Cl | O | H | $CH_3$ | $C(O)SCH_3$ | 4 |
| 33 | F | Cl | O | H | $CH_3$ | $C(O)SCH(CH_3)_2$ | 4 |
| 34 | F | Cl | O | H | $CH_3$ | $C(O)O-N=C(CH_3)_2$ | 4 |
| 35 | F | Cl | O | H | $CH_3$ | $C(O)OCH_2C\equiv CH$ | 4 |
| 36 | F | Cl | O | H | $CH_3$ | $C(O)OC(CH_3)_2C\equiv CH$ | 4 |
| 37 | F | Cl | O | H | $CH_3$ | $C(O)OCH_2CH=CH_2$ | 4 |
| 38 | F | Cl | O | H | $CH_3$ | $C(O)NHCH_2C\equiv CH$ | 4 |
| 39 | F | Cl | O | H | $CH_3$ | $CN$ | 4 |

Other representative compounds are identical with each of compounds 1–25, 32–39 above except that Q is at the 3-position. Still other representative compounds are identical with each of compounds 1–25, 32–39 except that Q is at the 2-position.

Other representative compounds are identical with each of the foregoing compounds except that in each case M is a nitrogen atom.

Still other representative compounds are identical with each of the foregoing compounds except that in each m is one and $R^{4a}$ is $CH_3$.

TABLE 2

PHYSICAL PROPERTIES

| Cmpd No. | Melting Point (°) | Empirical Formula | Elemental Analysis C | H | N |
|---|---|---|---|---|---|
| 1 | oil | $C_{25}H_{23}ClFNO_6$ | C 61.54 | 4.75 | 2.87 |
| | | | F 61.60 | 4.48 | 2.34 |
| 2 | 102–103 | $C_{24}H_{21}ClFNO_6$ | C 60.82 | 4.47 | 2.96 |
| | | | F 60.88 | 4.38 | 2.92 |
| 3 | oil | $C_{24}H_{23}ClFNO_6$ | C 60.56 | 4.83 | 2.94 |
| | | | F 60.03 | 4.34 | 2.85 |
| 4 | oil | $C_{25}H_{23}Cl_2FNO_6$ | C 59.53 | 4.59 | 2.77 |
| | | | F 59.66 | 4.86 | 2.75 |

TABLE 3

Pre-emergence Percent Control

| Compound No. | 1 | 2 | 3 | 4 |
|---|---|---|---|---|
| Rate (kg/ha) | 0.25 | 0.25 | 0.25 | 0.125 |
| Species | | | | |
| Cotton | 10 | 10 | 5 | 0 |
| Soybean | 20 | 20 | 20 | 0 |
| Field Corn | 10 | 5 | 0 | 0 |
| Rice | 10 | 10 | 10 | 5 |
| Wheat | 0 | 5 | 5 | 0 |
| Morningglory | 40 | 10 | 20 | 0 |
| Wild Mustard | 100 | 20 | 50 | 0 |
| Velvetleaf | 70 | 70 | 70 | 10 |
| Barnyardgrass | 10 | 10 | 0 | 10 |
| Green Foxtail | 5 | 0 | 0 | 20 |
| Johnsongrass | 30 | 10 | 0 | 10 |

TABLE 4

| | Post-emergence Percent Control | | | |
|---|---|---|---|---|
| Compound No. | 1 | 2 | 3 | 4 |
| Rate (kg/ha) | 0.0625 | 0.0625 | 0.0625 | 0.0125 |
| Species | | | | |
| Cotton | 100 | 100 | 100 | 100 |
| Soybean | 40 | 60 | 90 | 40 |
| Field Corn | 30 | 30 | 40 | 30 |
| Rice | 10 | 20 | 20 | 10 |
| Wheat | 10 | 40 | 40 | 20 |
| Morningglory | 100 | 100 | 100 | 100 |
| Wild Mustard | 80 | 80 | 100 | 100 |
| Velvetleaf | 100 | 100 | 100 | 100 |
| Barnyardgrass | 30 | 20 | 40 | 30 |
| Green Foxtail | 10 | 90 | 95 | 95 |
| Johnsongrass | 20 | 20 | 50 | 50 |

I claim:

1. Compound of the formula

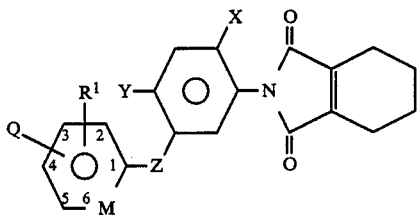

where Z is O, S, NH or alkylamino and Q is

—[O—CH($R^{4a}$)CO]$_m$—OCH($R^4$)$Q^2$;

$Q^2$ is —C(O)$R^3$ or —CN;

M is CH or N;

$R^4$ and $R^{4a}$ are independently H or $C_2H_5$ or $CH_3$;

$R^3$ is OH, alkoxy, alkylthio, alkenyloxy or alkynyloxy, amino, phenylamino, alkylamino, alkenylamino, alkynylamino, alkoxyamino or alkyl-, haloalkyl- or arylsulfonylamino of the formula —NHSO$_2R^5$ or —N(SO$_2R^5$)SO$_2R^6$, or an —O—N=$R^7$ radical where $R^7$ is alkylidene;

$R^5$ and $R^6$ are independently alkyl, haloalkyl or phenyl which is unsubstituted or substituted with alkoxy or halogen;

m is zero or 1;

$R^1$ is H, alkyl, halogen, haloalkyl, nitro, NH$_2$, alkoxy or alkylthio, or cyano;

X is H, halogen, alkyl, haloalkyl or nitro; and

Y is H, halogen, alkyl, alkoxy, haloalkyl, —SOCF$_3$ or halo lower alkoxy;

wherein the alkyl, alkenyl, alkynyl, or alkylene moieties are less than 6 carbon atoms.

2. Compound as in claim 1 in which m is zero and Z is O.

3. Compound as in claim 1 in which X is Cl or F and Y is Cl or Br.

4. Compound as in claim 2 in which X is F and Y is Cl or Br.

5. Compound as in claim 1 in which $Q^2$ is —C(O)$R^3$.

6. Compound as in claim 5 in which X is F or Cl and Y is Cl or Br.

7. Compound as in claim 5 in which $R^4$ is methyl, m is zero and Z is O.

8. Compound as in claim 7 in which $R^3$ is alkoxy of 1 to 3 carbon atoms.

9. An herbicidal composition containing an herbicidally effective amount of a compound of claim 1 in admixture with a suitable carrier.

10. An herbicidal composition containing an herbicidally effective amount of a compound of claim 8 in admixture with a suitable carrier.

11. A method of controlling weeds which comprises applying to the locus where control is desired an herbicidally effective amount of the composition of claim 9.

12. A method of controlling weeds which comprises applying to the locus where control is desired an herbicidally effective amount of the composition of claim 11.

* * * * *